United States Patent [19]

Morgan

[11] 4,454,120

[45] Jun. 12, 1984

[54] ANALGESIC DIPEPTIDE AMIDES AND METHOD OF USE AND COMPOSITIONS THEREOF

[75] Inventor: Barry A. Morgan, Albany, N.Y.

[73] Assignee: Sterling Drug Inc., New York, N.Y.

[21] Appl. No.: 423,055

[22] Filed: Sep. 24, 1982

Related U.S. Application Data

[63] Continuation-in-part of Ser. No. 286,672, Jul. 24, 1981, abandoned.

[51] Int. Cl.³ .................. A61K 37/00; C07C 103/52
[52] U.S. Cl. .......................... 424/177; 260/112.5 E
[58] Field of Search .............. 260/112.5 B, 112.5 R; 424/177

[56] References Cited

U.S. PATENT DOCUMENTS

| | | | |
|---|---|---|---|
| 4,127,535 | 11/1978 | Coy et al. | 260/112.5 R |
| 4,178,371 | 12/1979 | Morgan | 260/112.5 E |
| 4,261,883 | 4/1981 | Smolarsky | 260/112.5 E |
| 4,350,627 | 9/1982 | de Castiglione et al. | 260/112.5 E |
| 4,380,535 | 4/1983 | Sarantakis | 260/112.5 E |

OTHER PUBLICATIONS

McGregor et al., Life Sciences 23, 1371–1378 (1978).
Roques et al., European J. of Pharmacology 60, (1979) 109–110.

*Primary Examiner*—Delbert R. Phillips
*Attorney, Agent, or Firm*—Theodore C. Miller; Paul E. Dupont; B. Woodrow Wyatt

[57] ABSTRACT

A genus of dipeptide amides including as the preferred subgenus the dipeptide amides having the structural formula $R_1TyrR_2D-Q-NR_4R_5$ wherein Q is Met, Met(O), Gln or Ser, $R_1$ and $R_2$ are each hydrogen or alkyl, $R_4$ is phenylalkyl or substituted-phenylalkyl and $R_5$ is hydrogen, alkyl, phenylalkyl, substituted-phenylalkyl or X-alkyl wherein X is an electronegative group are prepared by condensing the dipeptide with the amine or the amino acid with the amino acid amide and are useful as analgesics.

39 Claims, No Drawings

ANALGESIC DIPEPTIDE AMIDES AND METHOD OF USE AND COMPOSITIONS THEREOF

CROSS-REFERENCE TO RELATED APPLICATION

This application is a continuation-in-part of my copending application Ser. No. 286,672 filed July 24, 1981 and now abandoned.

BACKGROUND OF THE INVENTION

1. Field of the Invention

The invention relates to dipeptide amides which are useful as analgesics.

2. Description of the Prior Art

Coy and Kastin U.S. Pat. No. 4,127,535 describes

H-Tyr-X-Y wherein: X is a chiral residue of a D-amino acid selected from the group consisting of D-alanine, D-leucine, D-isoleucine, D-valine, D-phenylalanine, D-tyrosine, D-trytophan, D-serine, D-threonine, D-methionine, D-glutamic acid, D-glutamine, D-proline[,] D-aspartic acid, D-asparagine, D-lysine, D-arginine and D-histidine; and Y is selected from the group consisting of hydroxy, amino, loweralkylamino, diloweralkylamino and lower alkoxy
which are stated to be
useful as analgesic, tranquilizer, sedative, hypnotic, anti-depressant[,] prolactin releasing and growth hormone releasing agents
and which are designated in the illustrative examples as derivatives of β-lipotropin fragment 61–62. Example 34 specifically describes D-Ala$^2$-β-lipotropin fragment 61–62 amide by name and method of preparation but does not describe any chemical or biological properties thereof.

McGregor (et al., Life Sciences, vol. 23, no. 13, pp. 1371–1378, 1978) describes H-Tyr-D-Ala-NH$_2$ (D-Ala$^2$-β-lipotropin fragment 61–62 amide) and shows that it is greater than 10 times less potent intravenously and 200 times less potent intraventricularly in the tail flick test for analgesia in the rat, and binds to the opiate receptor in rat brain membranes with 830 times less affinity, than morphine.

Roques (et al., European Journal of Pharmacology, vol. 60, pp. 109–110, 1979) describes HTyrD-AlaNH(CH$_2$)$_2$NH(CH$_2$)$_2$Phenyl, which was less then 1% as potent as Met-enkephalin in both the guinea pig ileum and mouse vas deferens tests.

SUMMARY OF THE INVENTION

In a composition of matter aspect the invention is 2-(L-N$^2$-R$_1$-N-R$_2$-tyrosylamino)-2-R$_3$-N-R$_4$-N-R$_5$-acetamide having the structural formula

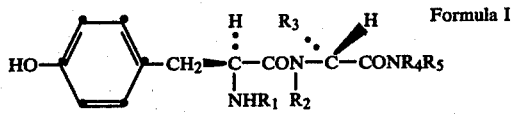

Formula I wherein

R$_1$ is hydrogen, alkyl of one to five carbon atoms, allyl, cyclopropylmethyl, formyl, acetyl or propionyl;

R$_2$ is hydrogen or alkyl of one to five carbon atoms;

R$_3$ is (CH$_2$)$_m$X wherein m is an integer from 1 through 4 and X is amino, methylamino, dimethylamino, dimethyloxoamino, acetamido, N-methylacetamido, methylthio, methylsulfinyl, methylsulfonyl, hydroxy, carboxy, carbamoyl, methylcarbamoyl, dimethylcarbamoyl, phenyl or phenyl substituted by fluoro, chloro, methyl, methoxy or trifluoromethyl;

R$_4$ is (CH$_2$)$_n$Y, wherein n is an integer from 2 through 10 and Y is phenyl or phenyl substituted by fluoro, chloro, methyl, methoxy or trifluoromethyl; and R$_5$ is hydrogen, alkyl of one to five carbon atoms, or is selected from the group consisting of (CH$_2$)$_m$X as defined for R$_3$ and (CH$_2$)$_n$Y as defined for R$_4$;

or a pharmaceutically acceptable acid addition salt thereof.

The compounds of Formula I are useful as analgesics.

In a first process aspect the invention is the process of preparing 2-(L-N$^2$-R$_1$-N-R$_2$-tyrosylamino)-2-R$_3$-N-R$_4$-N-R$_5$-acetamide of Formula I which comprises condensing the corresponding L-N-R$_1$-tyrosine with the corresponding 2-R$_2$NH-2-R$_3$-acetic acid to form the corresponding 2-(L-N$^2$-R$_1$-N-R$_2$-tyrosylamino)-2-R$_3$-acetic acid and then condensing said 2-(L-N$^2$-R$_1$-N-R$_2$-tyrosylamino)-2-R$_3$-acetic acid with the corresponding HNR$_4$R$_5$, concomitantly protecting and deprotecting the α-amino, tyrosyl phenolic hydroxyl and acetyl carboxyl groups as required.

In a second process aspect the invention is the process of preparing 2-(L-N$^2$-R$_1$-N-R$_2$-tyrosylamino)-2-R$_3$-N-R$_4$-N-R$_5$-acetamide of Formula I which comprises condensing the corresponding L-N-R$_1$-tyrosine with the corresponding 2-R$_2$NH-2-R$_3$-acetic acid methyl ester to form the corresponding 2-(L-N$^2$-R$_1$-N-R$_2$-tyrosylamino)-2-R$_3$-acetic acid methyl ester, then condensing said 2-(L-N$^2$-R$_1$-N-R$_2$-tyrosylamino)-2-R$_3$-acetic acid methyl ester with hydrazine to form 2-(L-N$^2$-R$_1$-N-R$_2$-tyrosylamino)-2-R$_3$-acetyl hydrazide, then reacting said 2-(L-N$^2$-R$_1$-N-R$_2$-tyrosylamino)-2-R$_3$-acetyl hydrazide with an alkyl nitrite to form 2-(L-N$^2$-R$_1$-N-R$_2$-tyrosylamino)-2-R$_3$-acetyl azide, then condensing said 2-(L-N$^2$-R$_1$-N-R$_2$-tyrosylamino)-2-R$_3$-acetyl azide with the corresponding HNR$_4$R$_5$, concomitantly protecting and deprotecting the α-amino and tyrosyl phenolic hydroxyl groups as required.

In a third process aspect the invention is the process of preparing 2-(L-N$^2$-R$_1$-N-R$_2$-tyrosylamino)-2-R$_3$-N-R$_4$-N-R$_5$-acetamide of Formula I which comprises condensing the corresponding 2-R$_2$NH-2-R$_3$-acetic acid with the corresponding HNR$_4$R$_5$ to form the corresponding 2-R$_2$NH-2-R$_3$-N-R$_4$-N-R$_5$-acetamide and then condensing said 2-R$_2$NH-2-R$_3$-N-R$_4$-N-R$_5$-acetamide with L-N-R$_1$-tyrosine, concomitantly protecting and deprotecting the α-amino and tyrosyl phenolic hydroxyl groups as required.

In a method of use aspect the invention is the method of producing analgesia in a mammal in pain which comprises administering to the mammal an analgesically effective amount of 2-(L-N$^2$-R$_1$-N-R$_2$-tyrosylamino)-2-R$_3$-N-R$_4$-N-R$_5$-acetamide of Formula I or a pharmaceutically acceptable acid addition salt thereof.

In another composition of matter aspect the invention is a pharmaceutical composition for producing analgesia in a mammal consisting essentially of an analgesically effective concentration of 2-(L-N$^2$-R$_1$-N-R$_2$-tyrosylamino)-2-R$_3$-N-R$_4$-N-R$_5$-acetamide of Formula I or a pharmaceutically acceptable acid addition salt thereof and a pharmaceutically acceptable vehicle.

When $R_1$, $R_2$ or $R_5$ of Formula I is alkyl of one to five carbon atoms, it can be any of the possible primary, secondary and tertiary alkyls of one to five carbon atoms, especially including methyl, ethyl, n-propyl, isopropyl, n-butyl, tert-butyl, n-pentyl and 3-methylbutyl.

In a preferred composition of matter aspect the invention is $N-R_1$-L-tyrosyl-$N^2-R_2$-$N-R_4$-$N-R_5$-D-Q-amide having the structural formula $$R_1TyrR_2\text{-}D\text{-}Q\text{-}NR_4R_5 \qquad \text{Formula II}$$

wherein Q is Met, Met(O), Gln or Ser, which is the compound of Formula I wherein $R_3$ is $(CH_2)_mX$ wherein m is 2 and X is methylthio, methylsulfinyl or carbamoyl or wherein m is 1 and X is hydroxy, respectively, or a pharmaceutically acceptable acid addition salt thereof.

In a most preferred composition of matter aspect the invention is the following compounds of Formula II, which are the free base forms of the examples whose preparation and biological properties ae described below.

| Compound of Formula II | Example |
|---|---|
| HTyrD-MetNH(CH$_2$)$_3$Ph | 1 |
| HTyrD-Met(0)NH(CH$_2$)$_3$Ph | 2 |
| HTyrD-MetNMe(CH$_2$)$_3$Ph | 3 |
| HTyrD-Met(0)NMe(CH$_2$)$_3$Ph | 4 |
| MeTyrD-MetNH(CH$_2$)$_3$Ph | 5 |
| MeTyrD-Met(0)NH(CH$_2$)$_3$Ph | 6 |
| HTyrMeD-MetNH(CH$_2$)$_3$Ph | 7 |
| HTyrMeD-Met(0)NH(CH$_2$)$_3$Ph | 8 |
| HTyrD-GlnNH(CH$_2$)$_3$Ph | 9 |
| HTyrD-SerNH(CH$_2$)$_3$Ph | 10 |

In Formula II and the foregoing formulas of specific compounds of Formula II
Tyr represents L-tyrosyl,
D-Met represents D-methionyl,
D-Met(O) represents S-oxy-D-methionyl,
D-Gln represents D-glutaminyl,
D-Ser represents D-seryl,
Me represents methyl, and
Ph represents phenyl.

The symbols Tyr, D-Met, D-Met(O), D-Gln and D-Ser do not include the N-terminal and C-terminal groups. H of HTyr or Me of MeTyr is the same as $R_1$ of Formula I when $R_1$ is hydrogen or methyl, Me of MeD-Met is the same as $R_2$ of Formula I when $R_2$ is methyl, H of NH or Me of NMe is the same as $R_5$ of Formula I when $R_5$ is hydrogen or methyl, and $R_1$, $R_2$, $R_4$, and $R_5$ are otherwise also the same as $R_1$, $R_2$, $R_4$ and $R_5$ of Formula I.

DETAILED DESCRIPTION OF THE INVENTION INCLUSIVE OF THE PREFERRED EMBODIMENTS

Preparation Of The Compounds

The protection, activation, condensation and deprotection steps required to prepare the compounds of Formula I are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and dipeptide intermediates can be formed and used with or without being isolated and include the acyl halides and pseudohalides, especially the acyl azides; the anhydrides, especially the mixed anhydrides and most especially the mixed anhydride with diphenylphosphinyl chloride, isobutyl chloroformate or pivalyl chloride; derivatives formed by addition reactions, especially using dicyclohexylcrbodimide; displaceable acyl derivatives of heterocyclic nitrogen; ring-openable activated heterocyclic systems; acylphosphonium derivatives; activated esters, especially N-hydroxysuccinimide, nitrophenyl and pentafluorophenyl esters; and polymeric (solid phase) derivatives.

It is necessary that the N-terminal α-amino function be protected during the amide forming steps. It is preferred but not essential that the tyrosyl phenolic hydroxyl also be protected. The preferred α-amino protecting groups are benzyloxycarbonyl (Z), which can be removed by catalytic hydrogenation using palladium as catalyst or by hydrogen bromide in acetic acid, and tert-butyloxycarbonyl (Boc), which can be removed by acidic cleavage, for example, with hydrogen chloride in a suitable solvent or trifluoroacetic acid. Benzyl (Bz) and tert-butyl (tBu) are the preferred tyrosyl phenolic hydroxyl protecting groups. Benzyl can be removed by catalytic hydrogenation using palladium as catalyst or by hydrogen bromide in acetic acid. tert-Butyl can be removed by acidic cleavage, for example, with hydrogen chloride in a suitable solvent or trifluoroacetic acid.

The C-terminal carboxyl group must be protected during the peptide forming step. In the first process aspect it is protected as the amide, which is, of course, not removed. In the second process aspect the methyl ester protects the carboxyl group during peptide bond formation and subsequently activates it for hydrazide bond formation. In the third process aspect the C-terminal carboxyl group can be protected as the carboxylate salt, the t-butyl ester, which can be removed by acidic cleavage, for example, with hydrogen chloride in a suitable solvent or trifluoroacetic acid, or the benzyl ester, which can be removed by catalytic hydrogenation using palladium as catalyst.

The unprotected and protected L-N-$R_1$-tyrosine, unprotected and protected 2-$R_2$NH-2-$R_3$-acetic acid, 2-$R_2$NH-2-$R_3$-acetic acid methyl ester and HNR$_4$R$_5$ starting materials are known classes of compounds. The individual compounds are commercially available or can be made by methods specifically or generally described in the chemical literature.

Besides being preparable by the three process aspects of the invention the compounds of Formulas I and II wherein $R_3$ or $R_5$ is $(CH_2)_mX$ and X is dimethyloxoamino, methylsulfinyl and methylsulfonyl can also be prepared by oxidation by known methods of the respective corresponding compounds of Formulas I and II wherein $R_3$ or $R_5$ is $(CH_2)_mX$ is dimethylamino and methylthio.

The acid addition salts of the compounds of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formula I and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophylization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), high pressure liquid chromatography (HPLC), thin layer chromatography (TLC) and/or amino acid analysis.

EXAMPLE 1

HTyrD-MetNH(CH$_2$)$_3$Ph

A. BocD-MetNH(CH$_2$)$_3$Ph

N-Methylmorpholine (2.2 ml.), then pivalyl chloride (2.46 ml.), were added to a solution of N-(tert-butyloxycarbonyl)-D-methionine (5.00 g.) in tetrahydrofuran (50 ml.) maintained at $-20°$ C., and the mixture was stirred for five minutes. 3-Phenylpropylamine (2.84 ml.) was then added. The mixture was stirred for two hours at $-15°$ C., then for 18 hours at room temperature, then stripped of solvent. A solution of the residue in ethyl acetate was washed twice with aqueous citric acid, twice with aqueous sodium bicarbonate and once with aqueous sodium chloride, dried and stripped of solvent. Recrystallization of the residue from ethyl acetate-hexane afforded N$^2$-(tert-butyloxycarbonyl)-N-(3-phenylpropyl)-D-methioninamide in two crops (5.50 g., 0.39 g.; $[\alpha]_D^{25} -12.7°$, c=1, dimethylformamide).

B. HD-MetNH(CH$_2$)$_3$Ph

A solution of N$^2$-(tert-butyloxycarbonyl)-N-(3-phenylpropyl)-D-methioninamide (1.75 g.) in acetic acid (10 ml.) and hydrogen chloride-ethyl acetate (4 N, 20 ml.) was stirred at room temperature for one hour, then stripped of volatiles under vacuum. A solution of the residue in ethyl acetate-ether was stripped of volatiles under vacuum, finally over phosphorous pentoxide and potassium hydroxide, affording N-(3-phenylpropyl)-D-methioninamide hydrochloride as a vicous oil (1.50 g.).

C. BocTyr(tBu)D-MetNH(CH$_2$)$_3$Ph

N-methylmorpholine (485 mg.), then a solution of pivalyl chloride (579 mg.) in tetrahydrofuran (5 ml.), were added to a solution of N-(tert-butyloxycarbonyl)-O-(tert-butyl)-L-tyrosine in tetrahydrofuran (35 ml.) maintained at $-20°$ C., and the mixture was stirred at that temperature for about 10 minutes. A solution of N-(3-phenylpropyl)-D-methioninamide (1.50 g.) and N-methylmorpholine (485 mg.) in tetrahydrofuran (60 ml.) was then added, and stirring was continued at $-20°$ C. for two hours and then at room temperature overnight. Ethyl acetate (150 ml.) was added. The mixture was washed three times with saturated aqueous sodium bicarbonate, three times with aqueous citric acid (5%), twice with water and twice with saturated aqueous sodium chloride, dried over magnesium sulfate and concentrated under vacuum. Crystallization of the residue from ethyl acetate-hexane afforded as a white solid [N-(tert-butyloxycarbonyl)-O-(tert-butyl)-L-tyrosyl]-N-(3-phenylpropyl)-D-methioninamide (680 mg.; m.r. 158°–159° C.; $[\alpha]_D^{25} +55.4°$, c=1 methanol).

D. HTyrD-MetNH(CH$_2$)$_3$Ph

A solution of [N-(tert-butyloxycarbonyl)-O-(tert-butyl)-L-tyrosyl]-N-(3-phenylpropyl)-D-methioninamide (610 mg.) in hydrogen chloride-dioxane (3.9 N, 10 ml.) was stirred at room temperature for 40 minutes, then concentrated under vacuum. Ether was added to the residue, the solution was concentrated under vacuum, and the process was repeated. A solution of the residue (502 mg.) in water (20 ml.) was filtered and lyophilized, affording as an amorphous off-white solid L-tyrosyl-N-(3-phenylpropyl)-D-methioninamide monohydrochloride monohydrate (473 mg.), whose free base is the compound of Formula II wherein Q is Met, R$_1$, R$_2$ and R$_5$ are each hydrogen and R$_4$ is (CH$_2$)$_n$Y wherein n is 3 and Y is phenyl.

EXAMPLE 2

HTyrD-Met(O)NH(CH$_2$)$_3$Ph

A solution of L-tyrosyl-N-(3-phenylpropyl)-D-methioninamide monohydrochloride monohydrate (219 mg.) and aqueous hydrogen peroxide (3%, 640 μl) in acetic acid (5 ml.) was stirred at room temperature for two and one quarter hours, then concentrated under vacuum. The residue was reevaporated under vacuum once from ethyl acetate and three times from ether. A solution of the residue in water was filtered and lyophilized, affording as an amorphous white solid L-tyrosyl-N-(3-phenylpropyl)-D-methioninamide S-oxide monohydrochloride sesquihydrate (225 mg.), whose free base is the compound of Formula II wherein Q is Met(O), R$_1$, R$_2$ and R$_5$ are each hydrogen and R$_4$ is (CH$_2$)$_n$Y wherein n is 3 and Y is phenyl.

EXAMPLE 3

HTyrD-MetNMe(CH$_2$)$_3$Ph

A. BocD-MetNMe(CH$_2$)$_3$Ph

Triethylamine (1.48 ml.), then isobutyl chloroformate (1.43 ml.), were added to a solution of N-(tert-butyloxycarbonyl)-D-methionine (2.64 g.) in tetrahydrofuran (50 ml.) maintained at $-10°$ C., and the mixture was stirred for ten minutes. A solution of N-methyl-3-phenylpropylamine hydrochloride (1.97 g.) and triethylamine (1.48 ml.) in tetrahydrofuran (50 ml.) was then added. The mixture was allowed to rise to room temperature during two hours, filtered and concentrated. A solution of the residue in ethyl acetate was washed with water, aqueous citric acid (5%), aqueous sodium chloride and aqueous sodium bicarbonate, dried and stripped of solvent, affording N$^2$-(tert-butyloxycarbonyl)-N-methyl-N-(3-phenylpropyl)-D-methioninamide as an orange syrup (4.06 g.).

B. HD-MetNMe(CH$_2$)$_3$Ph

A solution of N$^2$-(tert-butyloxycarbonyl)-N-methyl-N-(3-phenylpropyl)-D-methioninamide (4.06 g.) in hydrogen chloride-ethyl acetate (3.9 N, 20 ml.) was stirred at room temperature for 40 minutes. Ether (100 ml.) was added, precipitating an oil, and the mixture was stripped of volatiles under vacuum, affording N-methyl-N-(3-phenylpropyl)-D-methioninamide (3.13 g.).

C. BocTyr(tBu)D-MetNMe(CH₂)₃Ph

By the method of part A of this sample N-(tert-butyloxycarbonyl)-O-(tert-butyl)-L-tyrosine (2.59 g.) was condensed with N-methyl-N-(3-phenylpropyl)-D-methioninamide (1.4 g.). The product was crystallized twice from ethyl acetate, affording [N-(tert-butyloxycarbonyl)-O-(tert-butyl)-L-tyrosyl]-N-methyl-N-(3-phenylpropyl)-D-methioninamide (810 mg., m.r. 130°–131° C.).

D. HTyrD-MetNMe(CH₂)₃Ph

A solution of [N-(tert-butyloxycarbonyl)-O-(tert-butyl)-L-tyrosyl]-N-methyl-N-(3-phenylpropyl)-D-methioninamide (601 mg.) in hydrogen chloride-ethyl acetate (3.9 N, 5 ml.) was stirred at room temperature for one hour, then concentrated. The residue was purified by reverse phase high pressure liquid chromatography on octadecylsilated silica gel (350 g.) using ammonium acetate (0.15%) in methanol-water (3:2) as the eluant (200 ml./min.). A solution of the product, which appeared in fraction 3 ($k' = 3.75$–$5.75$), in hydrochloric acid (0.0936N, 20 ml.) and water (20 ml.) was lyophilized. The product was twice more lyophilized, affording as an amorphous white solid L-tyrosyl-N-methyl-N-(3-phenylpropyl)-D-methioninamide monohydrochloride (0.21 g.), whose free base is the compound of Formula II wherein Q is Met, $R_1$ and $R_2$ are each hydrogen, $R_4$ is $(CH_2)_nY$ wherein n is 3 and Y is phenyl and $R_5$ is methyl.

EXAMPLE 4

HTyrD-Met(O)NMe(CH₂)₃Ph

A solution of L-tyrosyl-N-methyl-N-(3-phenylpropyl)-D-methioninamide monohydrochloride (1.3 g.) and aqueous hydrogen peroxide (3%, 2.7 ml.) in acetic acid (10 ml.) was stirred at room temperature for two hours, the concentrated. The residue was evaporated twice from ethyl acetate then purified by reverse phase high pressure liquid chromatography on octadecylsilated silica gel (350 g.) using ammonium acetate (0.15%) in methanol-water (3:2) as the eluant (200 ml./min.). A solution of the product (1.0 g.), which appeared in fraction 2 ($k' = 1.4$–$3.0$), in hydrochloric acid (0.0936N, 30 ml.) and water (30 ml.) was lyophilized, affording L-tyrosyl-N-methyl-N-(3-phenylpropyl)-D-methioninamide S-oxide monohydrochloride monohydrate ($[\alpha]_D^{25} + 61.4°$, c=1, methanol), whose free base is the compound of Formula II wherein Q is Met(O), $R_1$ and $R_2$ are each hydrogen, $R_4$ is $(CH_2)_nY$ wherein n is 3 and Y is phenyl and $R_5$ is methyl.

EXAMPLE 5

MeTyrD-MetNH(CH₂)₃Ph

A. BocMeTyr(tBu)D-MetNH(CH₂)₃Ph

Diisopropylethylamine (0.90 ml.), then diphenylphosphinyl chloride (1.23 g.), were added to a solution of N-(tert-butyloxycarbonyl)-O-(tert-butyl)-N-methyl-L-tyrosine (1.76 g.) in tetrahydrofuran (15 ml.) maintained at −20° C., and the mixture was stirred for ten minutes. A solution of N-(3-phenylpropyl)-D-methioninamide hydrochloride (1.58 g.) and diisopropylethylamine (0.90 ml.) in tetrahydrofuran (10 ml.) was then added. The mixture was stirred for one half hour at −20°, one hour at 0° C. and overnight at room temperature, then filtered and stripped of solvent. A solution of the residue in ethyl acetate (100 ml.) was washed with water, aqueous citric acid, water again, aqueous sodium bicarbonate and water again, dried and stripped of solvent. Purification of the residue by high pressure liquid chromatography on silica gel (350 g.) using hexane-ethyl acetate (2:1) as the eluant afforded in fractions 6–7 ($k' = 8$–$14$) [N-(tert-butyloxycarbonyl)-O-(tert-butyl)-N-methyl-L-tyrosyl]-N-(3-phenylpropyl)-D-methioninamide as a clear gum (2.1 g.).

B. MeTyrD-MetNH(CH₂)₃Ph

A solution of [N-(tert-butyloxycarbonyl)-O-(tert-butyl)-N-methyl-L-tyrosyl]-N-(3-phenylpropyl)-D-methioninamide (1.9 g.) in hydrogen chloride-dioxane (3.9 N, 25 ml.) was stirred for 75 minutes at room temperature, then stripped of volatiles. Trituration of the residue with ether gave a white powder (1.308 g.), an aqueous solution of which was lyophilized, affording as an amorphous solid N-methyl-L-tyrosyl-N-(3-phenylpropyl)-L-methioninamide monohydrochloride hydrate (4:1) (1.260 g.; $[\alpha]_D^{25} + 68.0°$, c=1, methanol), whose free base is the compound of Formula II wherein Q is Met, $R_1$ is methyl, $R_2$ and $R_5$ are each hydrogen and $R_4$ is $(CH_2)_nY$ wherein n is 3 and Y is phenyl.

EXAMPLE 6

MeTyrD-Met(O)NH(CH₂)₃Ph

A solution of N-methyl-L-tyrosyl-N-(3-phenylpropyl)-D-methioninamide monohydrochloride hydrate (4:1) (690 mg.) and aqueous hydrogen peroxide (3%, 1.95 ml.) in acetic acid (10 ml.) was stirred at room temperature, then stripped of volatiles. The residue was purified by reverse phase high pressure liquid chromatography on octadecylsilated silica gel (350 g.) using ammonium acetate (0.2%) in methanol-water (1:1) as the eluant. A solution of the product, which appeared in fractions 4–5 (centered at $k' = 2.0$), in methanol (20 ml.) and hydrochloric acid (0.01 N, 100 ml.) was concentrated (to 60 ml.), filtered and lyophilized, affording as an amorphous solid N-methyl-L-tyrosyl-N-(3-phenylpropyl)-D-methioninamide S-oxide monohydrochloride hemihydrate (558 mg.; $[\alpha]_D^{25} + 59.8°$, c=1, methanol), whose free base is the compound of Formula II wherein Q is Met(O), $R_1$ is methyl, $R_2$ and $R_5$ are each hydrogen and $R_4$ is $(CH_2)_nY$ wherein n is 3 and Y is phenyl.

EXAMPLE 7

HTyrMeD-MetNH(CH₂)₃Ph

A. BocMeD-MetOH

A solution of N-(tert-butyloxycarbonyl)-D-methionine (20 g.) in tetrahydrofuran was added dropwise with stirring to a suspension of potassium hydride (35% in mineral oil, 27.5 g.) in tetrahydrofuran (160 ml.) containing 18-crown-6 ether (1 g.) maintained at ice bath temperature. Stirring was continued for one and one quarter hours. Methyl iodide (5 ml.) was added, stirring was continued, and the temperature was allowed to rise to room temperature during 22 hours. The pH was adjusted to 3 with aqueous citric acid (1 M) with cooling. The mixture was partitioned between ether and water. The ether layer was extracted with aqueous sodium bicarbonate. The aqueous sodium bicarbonate layer was extracted with ether. The latter ether layer was washed with water, dried and stripped of ether, affording N-(tert-butyloxycarbonyl)-N-methyl-D-methionine as a syrup (15.5 g.).

B. BocMeD-MetNH(CH$_2$)$_3$Ph

By the method of part A of Example 5 and using triethylamine instead of diisopropylethylamine, N-(tert-butyloxycarbonyl)-N-methyl-D-methionine (6.6 g.) was condensed with 3-phenylpropylamine (3.4 g.) and the product (8.00 g.) was purified by high pressure liquid chromatography on silica gel (350 g.) using hexane-ethyl acetate (3:1) as the eluant, affording N$^2$-(tert-butyloxycarbonyl)-N$^2$-methyl-N-(3-phenylpropyl)-D-methioninamide as a pale yellow syrup in two parts (3.43 g., 3.0 g.).

C. MeD-MetNH(CH$_2$)$_3$Ph

A solution of N$^2$-(tert-butyloxycarbonyl)-N$^2$-methyl-N-(3-phenylpropyl)-D-methioninamide (3.3 g.) in hydrogen chloride-ethyl acetate (3.4 N, 18 ml.) was stirred for one half hour at room temperature, then stripped of volatiles, affording N$^2$-methyl-N-(3-phenylpropyl)-D-methioninamide hydrochloride as a crystalline solid (2.5 g., m.r. 107°–110° C.).

D. BocTyr(tBu)MeD-MetNH(CH$_2$)$_3$Ph

By the method of part A of Example 5 and using triethylamine instead of diisopropylethylamine and chloroform as a cosolvent with tetrahydrofuran, N-(tert-butyloxycarbonyl)-O-(tert-butyl)-L-tyrosine (2.13 g.) was condensed with N$^2$-methyl-N-(3-phenylpropyl)-D-methioninamide hydrochloride (2.0 g.). The product, [N-(tert-butyloxycarbonyl)-O-(tert-butyl-L-tyrosyl]-N$^2$-methyl-N-(3-phenylpropyl)-D-methioninamide, was purified by crystallization, the first crop (1.51 g., m.r. 129°–130° C.) from ethyl acetate, the second crop (0.53 g.) from ethyl acetate-hexane.

E. HTyrMeD-MetNH(CH$_2$)$_3$Ph

A solution of [N-(tert-butyloxycarbonyl)-O-(tert-butyl)-L-tyrosyl]-N$^2$-methyl-N-(3-phenylpropyl)-D-methioninamide (1.81 g.) in hydrogen chloride-ethyl acetate (3.4 N, 20 ml.) was stirred for one hour at room temperature, then stripped of volatiles. The product was crystallized from isopropyl alcohol, affording L-tyrosyl-N$^2$-methyl-N-(3-phenylpropyl)-D-methioninamide monohydrochloride (966 mg.; m.r. 208°–210° C.; $[\alpha]_D^{25}$+85.7°, c=1, methanol), whose free base is the compound of Formula II wherein Q is Met, R$_1$ and R$_5$ are each hydrogen, R$_2$ is methyl and R$_4$ is (CH$_2$)$_n$Y wherein n is 3 and Y is phenyl.

EXAMPLE 8

HTyrMeD-Met(O)NH(CH$_2$)$_3$Ph

A solution of L-trysoyl-N$^2$-methyl-N-(3-phenylpropyl)-D-methioninamide hydrochloride (280 mg.) and aqueous hydrogen peroxide (3%, 0.7 ml.) in acetic acid (5 ml.) was stirred at room temperature for two hours, then concentrated. An aqueous solution of the residue was filtered and lyophilized, affording as an amorphous white solid L-tyrosyl-N$^2$-methyl-N-(3-phenylpropyl)-D-methioninamide S-oxide monhydrochloride monohydrate (199 mg., $[\alpha]_D^{25}$+46.4°, c=1, methanol), whose free base is the compound of Formula II wherein Q is Met(O), R$_1$ and R$_5$ are each hydrogen, R$_2$ is methyl and R$_4$ is (CH$_2$)$_n$Y wherein n is 3 and Y is phenyl.

EXAMPLE 9

HTyrD-GlnNH(CH$_2$)$_3$Ph

A. BocD-GlnNH(CH$_2$)$_3$Ph

A solution of N-(tert-butyloxycarbonyl)-D-glutamine p-nitrophenyl ester (2.0 g.) and 3-phenylpropylamine (0.736 g.) in dimethylformamide (15 ml.) was stirred at room temperature for one hour, then concentrated under vacuum. A solution of the residue in ethyl acetate was washed once with water, twice with aqueous citric acid (5%), once again with water, five times with aqueous sodium hydroxide (1 N) and once with saturated aqueous sodium chloride, dried over magnesium sulfate and stripped of ethyl acetate. The residue was purified by high pressure liquid chromatography on silica gel (350 g.) using ethyl acetate-ethanol (98:2) as the eluant. The product was crystallized from ethyl acetate, affording N$^2$-(tert-butyloxycarbonyl)-N$^1$-(3-phenylpropyl)-D-glutamamide (1.76 g., m.r. 126°–218° C.).

B. BocTyr(tBu)D-GlnNH(CH$_2$)$_3$Ph

A solution of N$^2$-(tert-butyloxycarbonyl)-N$^1$-(3-phenylpropyl)-D-glutamamide (1.5 g.) in hydrogen chloride-dioxane (4.5 N, 10 ml.) was stirred at room temperature for 15 minutes. Water (50 ml.) was added and the mixture was concentrated to about 5 ml. Ethanol (50 ml.) was added and the mixture was concentrated to less than 5 ml. Dimethylformamide (20 ml.) was added and the mixture was stripped of the remaining ethanol, affording N$^1$-(3-phenylpropyl)-D-glutamamide hydrochloride as a solution in the dimethylformamide. N-(tert-Butyloxycarbonyl)-O-(tert-butyl)-L-tyrosine pentafluorophenyl ester (2.08 g.) and diisopropylethylamine (0.72 ml.) were added and the mixture was stirred at room temperature for two hours. More diisopropylethylamine was added to neutralize the mixture. The reaction was complete in one half hour. The mixture was stripped of volatiles under vacuum. A solution of the residue in ethyl acetate was washed twice with water, twice with saturated aqueous sodium bicarbonate, once again with water, twice with aqueous citric acid and once with saturated aqueous sodium chloride, dried and stripped of ethyl acetate. Methanol was added to the residue and the mixture was stripped again. The product (1.80 g.) was purified by high pressure liquid chromatography using ethyl acetate-ethanol (96:4) as the eluant, affording [N-(tert-butyloxycarbonyl)-O-(tert-butyl)-L-tyrosyl]-N$^1$-(3-phenylpropyl)-D-glutamamide as a gel in two crops (711 mg., 427 mg.).

C. HTyrD-GlnNH(CH$_2$)$_3$Ph

A solution of [N-(tert-butyloxycarbonyl)-O-(tert-butyl)-L-tyrosyl]-N$^1$-(3-phenylpropyl)-D-glutamamide (700 mg.) in acetic acid saturated with hydrogen chloride (15 ml.) was stirred at room temperature for one hour, then stripped of volatiles under vacuum at 40° C. An aqueous solution of the residue was filtered and lyophilized, affording as an amorphous white solid L-tyrosyl-N$^1$-(3-phenylpropyl)-D-glutamamide monohydrochloride hydrate (4:3) (545 mg.; $[\alpha]_D^{25}$+46.4°, c=1, methanol), whose free base is the compound of Formula II wherein Q is Gln, R$_1$, R$_2$ and R$_5$ are each hydrogen and R$_4$ is (CH$_2$)$_n$Y wherein n is 3 and Y is phenyl.

EXAMPLE 10

HTyrD-SerNH(CH$_2$)$_3$Ph

A. BocD-SerNH(CH$_2$)$_3$Ph

A solution of dicyclohexylcarbodiimide (5.16 g.) in tetrahydrofuran (15 ml.) was added with stirring to a solution of N-(tert-butyloxycarbonyl)-D-serine dicyclohexylamine salt (8.58 g.) and N-hydroxysuccinimide (2.56 g.) in tetrahydrofuran (60 ml.) maintained at 0° C. Stirring was continued at 0° C. for 15 minutes, then the temperature was allowed to rise to room temperature during one half hour. 3-Phenylpropylamine (3.00 g.) was added and the mixture was stirred at room temperature for 24 hours. The mixture was filtered and the filtrate was stripped of volatiles. A solution of the residue in ethyl acetate was washed with water, saturated aqueous sodium bicarbonate, water again, aqueous citric acid (5%) and saturated aqueous sodium chloride, dried over magnesium sulfate and stripped of ethyl acetate. The residue was purified by high pressure liquid chromatography on silica gel (350 g.) using ethyl acetate-hexane (2:1) as the eluant, and the product was crystallized from isopropyl acetate-hexane, affording N$^2$-(tert-butyloxycarbonyl)-N-(3-phenylpropyl)-D-serinamide (4.2 g.; m.r. 70°–72°; $[\alpha]_D^{25}+7.1°$, c=1, dimethylformamide).

B. HD-SerNH(CH$_2$)$_3$Ph

A solution of N$^2$-(tert-butyloxycarbonyl)-N-(3-phenylpropyl)-D-serinamide (3.93 g.) in acetic acid saturated with hydrogen chloride (50 ml.) was stirred at room temperature for one half hour, then stripped of volatiles. The residue was purified by column chromatography on silica gel (100–200 mesh, 200 g.) using ethyl acetate-pyridine-acetic acid-water (200:54:16:30) as the eluant, affording N-(3-phenylpropyl)-D-serinamide hydrochloride (1.14 g., m.r. 97°–102° C.).

C. ZTyr(Bz)D-SerNH(CH$_2$)$_3$Ph

A solution of N-benzyloxycarbonyl-O-benzyl-L-tyrosine pentafluorophenyl ester (2.34 g.), N-(3-phenylpropyl)-D-serinamide hydrochloride (1.00 g.) and diisopropylethylamine (0.71 ml.) in tetrahydrofuran (25 ml.) was stirred at room temperature for one hour. The mixture was triturated with water, and the product was precipitated with hot ethyl acetate and recrystallized from ethyl acetate, affording (N-benzyloxycarbonyl-O-benzyl-L-tyrosyl)-N-(3-phenylpropyl)-D-serinamide (1.35 g., m.r. 175°–177° C.).

D. HTyrD-SerNH(CH$_2$)$_3$Ph

A mixture of (N-benzyloxycarbonyl-O-benzyl-L-tyrosyl)-N-(3-phenylpropyl)-D-serinamide (1.25 g.), acetic acid (125 mg.) and palladium on carbon (10%, 100 mg.) in methanol (50 ml.) was hydrogenated under pressure for 30 hours, then filtered. The filtrate was stripped of volatiles. The residue was purified by reverse phase high pressure liquid chromatography on octadecylsilated silica gel (350 g.) using ammonium acetate (0.2%) in methanol-water (1:1) as the eluant, and an aqueous solution of the product was lyophilized, affording as an amorphous white solid L-tyrosyl-N-(3-phenylpropyl)-D-serinamide hydrate (3:2) (245 mg.; $[\alpha]_D^{25}+16.9°$, c=1, methanol), whose unsolvated form is the compound of Formula II wherein Q is Ser, R$_1$, R$_2$ and R$_5$ are each hydrogen and R$_4$ is (CH$_2$)$_n$Y wherein n is 3 and Y is phenyl.

BIOLOGICAL PROPERTIES OF THE COMPOUNDS

As stated above the compounds of Formula I are useful as analgesic agents. This utility has been shown by the results of testing the examples in vitro in the guinea pig ileum test. Some of the examples have also been shown to be active in vivo in the mouse acetylcholine writhing test.

Guinea Pig Ileum Test

Adult male guinea pigs (Charles River, Hartley strain) weighing 300–500 g. are decapitated, and the terminal ileum is exposed by reflecting the overlying cecum, severed at the ileocecal juncture, and removed while cutting the mesenteric attachments to avoid excessive traction on the tissue. The ileum (about 30 cm. in length) is transferred to a beaker containing warm modified Krebs-Henseleit solution (118 mM sodium chloride, 4.75 mM potassium chloride, 2.54 mM calcium chloride, 1.19 mM potassium dihydrogen phosphate, 1.2 mM magnesium sulfate, 25 mM sodium bicarbonate, 11 mM glucose, 20 $\mu$M choline chloride and 0.125 $\mu$M pyrilamine maleate). The terminal (aboral) portion (about 10 cm. in length) is discarded, and segments (3–4 cm. in length) are cut from the remainder and gently slid onto a glass rod (5–6 mm. in diameter) and arranged so that the meseneteric attachment is in a straight line. A cotton swab moistened in the solution is then carefully used to separate the longitudinal muscle from the underlying circular muscle. The longitudinal muscle and adhering myenteric plexus is then gently removed from the remaining tissue with forceps.

Strips of this prepared longitudinal muscle are mounted in a double-jacketed organ bath (5 ml.) under tension (1.0 g.), connected to isometric transducers (Grass FT .03), bathed in the modified Krebs-Henseleit solution described above, aerated with oxygen-carbon dioxide (95:5) and maintained at 37° C.

Stimulators (Grass S-44) are set to deliver repetitive monophasic square wave field stimulation (supramaximal voltage, 0.10 Hz., 0.25 msec. duration) through platinum ring electrodes at the top and bottom of the bath. Regular contractions of the muscle, which result from electrically-induced liberation of acetylcholine from postganglionic parasympathetic nerves, are recorded on a polygraph (Grass model 5). Following tissue equilibration (45–60 min.) and repeated washing (every 10 min.) an aqueous solution of a reference or test compound is added to the bath in a microliter volume (1.25–250 $\mu$l) and reductions in muscle twitch height are recorded. More compound can be added with (single dose method) or without (cumulative dose method) first washing the preparation.

From the results a half-mazimal inhibitory concentration (IC50) value for the compound is computed by regression analysis of a linear plot of logarithm of concentration against percent of inhibition of twitch height (probits). The ratio of the IC50 value of a reference compound to that of a test compound tested in the same preparation is the molar potency ratio. Usually four preparations are tested simultaneously by the same person (N=4), and the resulting four molar potency ratios are averaged.

The following results were obtained using the examples as test compounds and Met$^5$-enkephalin as the reference compound.

| Compound | Average Molar Potency Ratio |
|---|---|
| Met[5]-enkephalin | 100 |
| Example 1 | 279 |
| Example 2 | 1180 |
| Example 3 | 19 |
| Example 4 | 5 |
| Example 5 | 180 |
| Example 6 | 360 |
| Example 7 | 260 |
| Example 8 | 650 |
| Example 9 | 47 |
| Example 10 | 15 |

Mouse Acetylcholine Writhing Test

Male Swiss-Webster mice each weighing 18–24 g. are treated subcutaneously (10 ml./kg. injection volume) or orally with the test compound in an aqueous vehicle. Twenty minutes thereafter each mouse is injected intraperitoneally with acetylcholine (3.2 mg./kg.) in aqueous sodium chloride (0.9%). This dose of acetylcholine causes one or more characteristic writhes in the two minute period following injection in control mice which receive the aqueous vehicle not containing the test compound. A mouse not exhibiting the writhe during the two minute period is scored inhibited by the test compound. Test compounds are screened at doses of 100 and 30 mg./kg. subcutaneously and 300 and 100 mg./kg. orally using 15 mice at each dose level. ED50 values for active compounds are estimated by probit analysis of quantal scores at four or more dose levels using 15 mice at each dose level.

The compound of Example 5 showed a subcutaneous ED50 value of 8.5 mg./kg. with 95% confidence limits of 5.0–12 mg./kg. in this test.

Approximate ED50 values were determined subcutaneously for some of the other examples and are shown in the following table.

| Compound | ED50 (mg./kg.) |
|---|---|
| Example 1 | >30 |
| Example 2 | <20>10 |
| Example 4 | >30 |

To carry out the method of use and pharmaceutical composition aspects of the invention the compounds of Formula I can be administered orally or parenterally in liquid or solid dosge form as solutions, suspensions, emulsions, capsules or tablets, which are prepared with conventional pharmaceutical vehicles and adjuncts by conventional pharmaceutical techniques.

I claim:

1. 2-(L-$N^2$-$R_1$-N-$R_2$-tyrosylamino)-2-$R_3$-N-$R_4$-N-$R_5$-acetamide having the structural formula

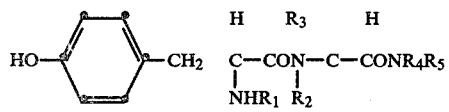

wherein $R_1$ is hydrogen, alkyl of one to five carbon atoms, allyl, cyclopropylmethyl, formyl, acetyl or propionyl;

$R_2$ is hydrogen or alkyl of one to five carbon atoms;

$R_3$ is $(CH_2)_mX$ wherein m is an integer from 1 through 4 and X is amino, methylamino, dimethylamino, dimethyloxoamino, acetamido, N-methylacetamido, methylthio, methylsulfinyl, methylsulfonyl, hydroxy, carboxy, carbamoyl, methylcarbamoyl, dimethylcarbamoyl, phenyl or phenyl substituted by fluoro, chloro, methyl, methoxy or trifluoromethyl;

$R_4$ is $(CH_2)_nY$, wherein n is an integer from 2 through 10 and Y is phenyl or phenyl substituted by fluoro, chloro, methyl, methoxy or trifluoromethyl; and $R_5$ is hydrogen, alkyl of one to five carbon atoms, or is selected from the group consisting of $(CH_2)_mX$ as defined for $R_3$ and $(CH_2)_nY$ as defined for $R_4$;

or a pharmaceutically acceptable acid addition salt thereof.

2. N-$R_1$-L-Tyrosyl-$N^2$-$R_2$-N-$R_4$-N-$R_5$-D-Q-amide having the structural formula

wherein Q is Met, Met(O), Gln or Ser, which is the compound according to claim 1 wherein $R_3$ is $(CH_2)_mX$ wherein m is 2 and X is methylthio, methylsulfinyl or carbamoyl or wherein m is 1 and X is hydroxy, respectively, or a pharmaceutically acceptable acid addition salt thereof.

3. A compound according to claim 2 wherein $R_4$ is $(CH_2)_nY$ wherein n is 3 and Y is phenyl.

4. A compound according to claim 3 wherein Q is Met or a pharmaceutically acceptable acid addition salt thereof.

5. A compound according to claim 4 wherein $R_1$ is hydrogen or a pharmaceutically acceptable acid addition salt thereof.

6. A compound according to claim 5 wherein $R_2$ is hydrogen or a pharmaceutically acceptable acid addition salt thereof.

7. The compound according to claim 6 wherein $R_5$ is hydrogen or a pharmaceutically acceptable acid addition salt thereof.

8. L-Tyrosyl-N-(3-phenylpropyl)-D-methioninamide monohydrochloride monohydrate according to claim 7.

9. The compound according to claim 6 wherein $R_5$ is methyl or a pharmaceutically acceptable acid addition salt thereof.

10. L-Tyrosyl-N-methyl-N-(3-phenylpropyl)-D-methioninamide monohydrochloride according to claim 9.

11. A compound according to claim 5 wherein $R_2$ is methyl or a pharmaceutically acceptable acid addition salt thereof.

12. The compound according to claim 11 wherein $R_5$ is hydrogen or a pharmaceutically acceptable acid addition salt thereof.

13. L-Tyrosyl-$N^2$-methyl-N-(3-phenylpropyl)-D-methioninamide monohydrochloride according to claim 12.

14. A compound according to claim 4 wherein $R_1$ is methyl or a pharmaceutically acceptable acid addition salt thereof.

15. A compound according to claim 14 wherein $R_2$ is hydrogen or a pharmaceutically acceptable acid addition salt thereof.

16. The compound according to claim 15 wherein $R_5$ is hydrogen or a pharmaceutically acceptable acid addition salt thereof.

17. N-Methyl-L-tyrosyl-N-(3-phenylpropyl)-D-methioninamide monohydrochloride hydrate (4:1) according to claim 16.

18. A compound according to claim 3 wherein Q is Met(O) or a pharmaceutically acceptable acid addition salt thereof.

19. A compound according to claim 18 wherein $R_1$ is hydrogen or a pharmaceutically acceptable acid addition salt thereof.

20. A compound according to claim 19 wherein $R_2$ is hydrogen or a pharmaceutically acceptable acid addition salt thereof.

21. The compound according to claim 20 wherein $R_5$ is hydrogen or a pharmaceutically acceptable acid addition salt thereof.

22. L-Tyrosyl-N-(3-phenylpropyl)-D-methioninamide S-oxide monohydrochloride sesquihydrate according to claim 21.

23. The compound according to claim 20 wherein $R_5$ is methyl or a pharmaceutically acceptable acid addition salt thereof.

24. L-Tyrosyl-N-methyl-N-(3-phenylpropyl)-D-methioninamide S-oxide monohydrochloride monohydrate according to claim 23.

25. A compound according to claim 19 wherein $R_2$ is methyl or a pharmaceutically acceptable acid addition salt thereof.

26. The compound according to claim 25 wherein $R_5$ is hydrogen or a pharmaceutically acceptable acid addition salt thereof.

27. L-Tyrosyl-$N^2$-methyl-N-(3-phenylpropyl)-D-methioninamide S-oxide monohydrochloride monohydrate according to claim 26.

28. A compound according to claim 18 wherein $R_1$ is methyl or a pharmaceutically acceptable acid addition salt thereof.

29. A compound according to claim 28 wherein $R_2$ is hydrogen or a pharmaceutically acceptable acid addition salt thereof.

30. The compound according to claim 29 wherein $R_5$ is hydrogen or a pharmaceutically acceptable acid addition salt thereof.

31. N-Methyl-L-tyrosyl-N-(3-phenylpropyl)-D-methioninamide S-oxide monohydrochloride hemihydrate according to claim 30.

32. A compound according to claim 3 wherein Q is Gln or a pharmaceutically acceptable acid addition salt thereof.

33. The compound according to claim 32 wherein $R_1$, $R_2$ and $R_5$ are each hydrogen or a pharmaceutically acceptable acid addition salt thereof.

34. L-Tyrosyl-$N^1$-(3-phenylpropyl)-D-glutamamide monohydrochloride hydrate (4:3) according to claim 33.

35. A compound according to claim 3 wherein Q is Ser or a pharmaceutically acceptable acid addition salt thereof.

36. The compound according to claim 35 wherein $R_1$, $R_2$ and $R_5$ are each hydrogen or a pharmaceutically acceptable acid addition salt thereof.

37. L-Tyrosyl-N-(3-phenylpropyl)-D-serinamide hydrate (3:2) according to claim 35.

38. The method of producing analgesia in a mammal in pain which comprises administering to the mammal an analgesically effective amount of 2-(L-$N^2$-$R_1$-N-$R_2$-tyrosylamino)-2-$R_3$-N-$R_4$-N-$R_5$-acetamide according to claim 1 or a pharmaceutically acceptable acid addition salt thereof.

39. A pharmaceutical composition for producing analgesia in a mammal consisting essentially of an analgesically effective concentration of 2-(L-$N^2$-$R_1$-N-$R_2$-tyrosylamino)-2-$R_3$-N-$R_4$-N-$R_5$-acetamide according to claim 1 or a pharmaceutically acceptable acid addition salt thereof and a pharmaceutically acceptable vehicle.

* * * * *

UNITED STATES PATENT AND TRADEMARK OFFICE
CERTIFICATE OF CORRECTION

PATENT NO. : 4,454,120
DATED : June 12, 1984
INVENTOR(S) : Barry A. Morgan

It is certified that error appears in the above-identified patent and that said Letters Patent is hereby corrected as shown below:

Cover page, item [75], "Albany" should read -- Colonie --.

Claim 1, column 13, line 60,

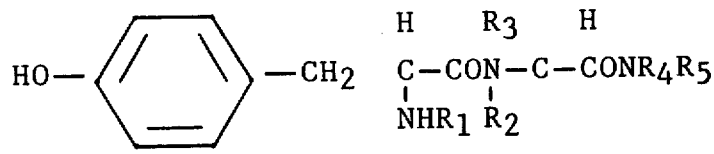

should read

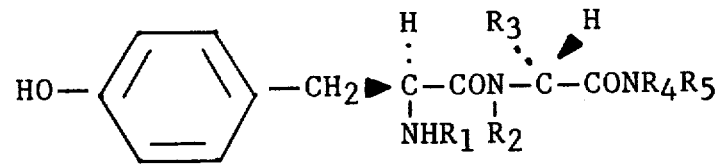

Signed and Sealed this

Eleventh Day of June 1985

[SEAL]

Attest:

DONALD J. QUIGG

Attesting Officer  Acting Commissioner of Patents and Trademarks